United States Patent
Richter et al.

(10) Patent No.: US 6,869,696 B2
(45) Date of Patent: Mar. 22, 2005

(54) ORGANIC RED ELECTRO-LUMINESCENT DEVICE INCLUDING A HETEROCYCLIC EMITTER

(75) Inventors: Andreas Richter, Ploessnitz (DE); Dietmar Keil, Wolfen (DE); Gerhard Diener, Koethen (DE)

(73) Assignee: Sensient Imaging Technologies GmbH (DE)

( * ) Notice: Subject to any disclaimer, the term of this patent is extended or adjusted under 35 U.S.C. 154(b) by 36 days.

(21) Appl. No.: 10/143,556

(22) Filed: May 10, 2002

(65) Prior Publication Data

US 2003/0228486 A1 Dec. 11, 2003

(51) Int. Cl.$^7$ ............................ H05B 33/14; C09K 11/06
(52) U.S. Cl. .................. 428/690; 428/917; 313/504; 313/506; 252/301.16; 548/190; 548/202; 549/396; 549/60; 549/385; 549/398; 549/414; 549/426
(58) Field of Search ................................. 428/690, 917; 313/504, 506; 252/301.16; 546/94; 549/396, 414, 424, 426, 398, 385, 60; 548/190, 202

(56) References Cited

U.S. PATENT DOCUMENTS

| | | | |
|---|---|---|---|
| 2,965,486 A | 12/1960 | Brooker et al. | ................ 96/105 |
| 3,511,831 A | 5/1970 | Dunbar et al. | ............... 260/240 |
| 3,852,683 A | 12/1974 | Webster et al. | ......... 331/94.5 L |

(List continued on next page.)

FOREIGN PATENT DOCUMENTS

| | | |
|---|---|---|
| DE | 23 45 189 | 3/1975 |
| DE | 23 45 189 A1 | 3/1975 |
| DE | 28 31 054 A1 | 1/1979 |
| DE | 689 19 989 T2 | 5/1995 |
| DE | 195 41 113 A1 | 4/1997 |
| EP | 0 244 051 A2 | 11/1987 |
| JP | 2001-019946 | * 1/2001 |

OTHER PUBLICATIONS

X. T. Tao, S. Miyata, H. Sasabe, G.J. Zhang, T. Wada, M.H. Jiang, "Efficient Organic Red Electrolumin Escent Device with Narrow Emission Peak," Applied Physics Letters, vol. 78, No. 3, Jan. 15, 2001, pp. 279–281.

C.W. Tang, "Organic Electrolumin Escent Diodes," Applied Physics Letters, vol. 51, No. 12, Sep. 21, 1987, pp. 913–915.

H. Katayama, M. Ohkoshi, "International Journal of Methods in Synthetic Organic Chemistry," 1982, pp. 692–693.

Kari Skinnemoen, Kjell Undheim, "Synthesis of 2H–Pyran–3–(6H)–ones," Acta Chemica Scandinavica, Series B, 1980, pp. 295–297.

S. Scheithauer et al, Darstellung substituierter Aminovinyl-verbindungen durch Umsetzung enthiolisierbarer Thiocarbonylverbindungen mit Aminen, Z. Chem, Feb. 9, 1968, pp. 181–182.

(List continued on next page.)

*Primary Examiner*—Dawn Garrett
(74) *Attorney, Agent, or Firm*—Foley & Lardner LLP

(57) ABSTRACT

The invention concerns an electro-luminescent device in which the luminescent layer contains a compound of general formula I as doping agent or as luminescent compound, whereby the radicals $R_1$ to $R_{12}$ are identical or are different, and mean hydrogen, straight chain or branched $C_1$–$C_6$ alkyl, aralkyl, aryl or substituted aryl; $R_1$ and $R_2$ and/or $R_3$ and $R_4$ and/or $R_4$ and $R_5$ and/or $R_5$ and $R_{11}$ and/or $R_8$ and $R_5$ and/or $R_4$ and $R_{12}$ can form an alicyclic, heterocyclic or aromatic ring; $R_5$ can furthermore be H, OH, $OR_9$, N,N-di-($C_1$–$C_6$) alkylamino, acetylamino or halogen; $R_6$ and $R_7$ together can form an alicyclic or heterocyclic ring; $A_1$ and $A_2$ are identical or different and are —CN, —$NO_2$ or —$COOR_8$; X is —CH, —$CR_{11}$ or N; and Y is O, —NH, —$NR_{12}$, S or Se. The doping agents together luminesce predominately red with very good quantum efficiency together with the luminescent compound as a function of concentration.

31 Claims, 2 Drawing Sheets

U.S. PATENT DOCUMENTS

| | | | |
|---|---|---|---|
| 4,047,948 A | | 9/1977 | Horgan ...................... 96/1.5 R |
| 4,145,215 A | * | 3/1979 | Van Allen et al. ................ 96/1 |
| 4,146,707 A | * | 3/1979 | Van Allen et al. .......... 542/433 |
| 4,175,960 A | | 11/1979 | Berwick et al. .............. 430/58 |
| 4,539,507 A | | 9/1985 | Van Slyke et al. .......... 313/504 |
| 4,769,292 A | | 9/1988 | Tang et al. ................. 428/690 |
| 5,061,569 A | | 10/1991 | VanSlyke et al. ........... 428/457 |
| 5,166,339 A | | 11/1992 | Duff et al. .................. 540/141 |
| 5,283,132 A | | 2/1994 | Ogura et al. ................ 428/690 |
| 5,359,072 A | | 10/1994 | Magnani et al. |
| 5,414,791 A | * | 5/1995 | Ermer et al. ................ 385/143 |
| 5,535,048 A | | 7/1996 | Magnani et al. |
| 5,561,733 A | * | 10/1996 | Ermer et al. ................ 385/143 |
| 5,708,178 A | * | 1/1998 | Ermer et al. ............. 546/276.7 |
| 5,908,581 A | | 6/1999 | Chen et al. ............ 252/301.16 |
| 5,935,720 A | | 8/1999 | Chen et al. ................. 428/690 |
| 6,020,078 A | | 2/2000 | Chen et al. ................. 428/690 |
| 6,025,894 A | | 2/2000 | Shirasaki et al. ............. 349/69 |
| 6,329,086 B1 | | 12/2001 | Shi et al. .................... 428/690 |
| 6,451,456 B1 | | 9/2002 | Kim et al. |
| 2002/0164498 A1 | | 11/2002 | Chen et al. |
| 2003/0044644 A1 | | 3/2003 | Kim et al. |
| 2003/0099861 A1 | | 5/2003 | Lee et al. |
| 2003/0162054 A1 | | 8/2003 | Chen et al. |
| 2003/0176520 A1 | | 9/2003 | Taniguchi et al. |

OTHER PUBLICATIONS

Lemke, Ralf, "Knoevenagel–Kondensationen in Dimethyl-formamid," *Synthesis*, (5), May, 1974, pp. 359–361.

Von Horst Hartmann, "Elektrophile Reaktionen am 2–Aminothiophensystem Darstellung und Eigenschaften von Substituierten Thienyl–aryl–methinen," Journal Für Praktische Chemie 36, Aug., 1967, pp. 50–72.

* cited by examiner

ORGANIC RED ELECTRO-LUMINESCENT DEVICE INCLUDING A HETEROCYCLIC EMITTER

The invention concerns an organic, especially red, electro-luminescent device, specifically, a device with a luminescent layer, containing at least one luminescent compound or, in addition, a new doping agent therefore, as well as new combinations.

Organic electro-luminescent compounds have been known for a some time now and consist, in the simplest cases, of a glass substrate with a transparent indium tin oxide coating (ITO), and a perforated transport layer, followed by a luminescent layer as well as a metal electrode with low electron affinity function (see FIG. 1).

Here, in the direction of passage of the metal electrode (cathode), mostly made of Ca or Mg by co-vaporization or sequential vaporization, for example, with Al or Ag, electrons and, from the transparent ITO contact (anode), holes (defect electrons) are injected into the organic interlaminar bonding. These recombine there and form singlet excitons which, after a short time under light emission, transition into the base state. The organic interlaminar bonding consists of a luminescent layer (the luminescent compound is also, at the same time, an electron conductor) and a hole transport layer. In the hole transport layer, N,N'-biphenyl-N,N'-bis-(m-tolyl)-benzidine (TPD) and N,N'-biphenyl-N,N'-bis-(1-naphthyl)-benzidine (1-NPB) are preferably used as hole transport materials. The additional attachment of an electron transport layer frequently leads to an increase in the quantum yield and/or to a reduction of the inception voltage of the electro-luminescent device (see FIG. 2).

At the same time, the luminescent layer can be designed to be very thin. By the use of luminescent material independently of its transport properties, the emission wave length can be selectively set over the entire visible spectral range.

Furthermore, one will obtain an improvement of the properties of the electro-luminescent device (increase in quantum yield and reduction of electro-luminescence inception voltage) if at least two hole transport layers, which are harmonized with each other, are used (see FIG. 3).

In some cases, an electron transport layer (as in FIG. 2) can additionally be installed in between the luminescent layer and the metal electrode.

Recently, an additional thin hole injection layer of, for example, CuPC (copper phthalocyanin) was vapor deposited between the transparent ITO and the hole transport layer to improve the properties of electro-luminescent devices (see FIG. 4).

In particular, so-called "star burst molecules" are used on account of their low ionization potential in the second hole transport layer. These are high level molecular compounds on the basis of triphenyl amine units.

Recently a new hole transport material was disclosed in DE-A-19,541,113 which, in addition to good hole transport properties, also possesses excellent layer-forming properties, a high thermal stability, and in this way a low recrystallization potential.

For the manufacture of full color capacity electro-luminescent devices, it is necessary to use red, green and blue electro-luminescent materials with high electro-luminescence quantum yield and color unity.

For a long time, tris-(8-hydroxyquinolino)-aluminum ($AlQ_3$) was used as a preferred illumination material in the luminescent layer (C. W. Tang, S. A. van Styke: Appl. Phys. Lett. 51, 1987, 913). This metal chelate complex luminescences, which themselves are green in the interlaminar bonding itself, wherein beryllium or gallium can also be used as metals in this complex.

Blue electro-luminescent devices are obtained through use of derivatives of 1,3,4-oxadiazoles or through the use of distyryl arylenes. Red luminescence radiation is achieved in particular through doping of $AlQ_3$ with 2-alkyl-6-N,N-dialkyl aminostyryl-substituted 4-dicyanomethylene-4H-pyrans, in particular, however, with 2-methyl-6-(4-N,N-dimethyl aminostyryl)-4-dicyanomethylene-4H-pyran (DCM) (U.S. Pat. No. 4,769,292), but also with quadratic acid color substances.

It should be mentioned as a disadvantage of the use of DCM as a doping agent of $AlQ_3$ that the emitted light appears as orange to the human eye, the efficiency of the emitted light is not sufficiently high for many applications owing to aggregation effects of the DCM dye in the $AlQ_3$, and the light-emitting diodes made with this do not operate with enough long term stability.

DCM (U.S. Pat. No. 3,852,683), already known as a laser dye, and other dyes correspondingly derived therefrom, represent formally conjugate polyenic combinations with a donor/acceptor substituent pattern. Through variation of the donor substituent in the dye molecule, as for example, through the exchange of the 4-N,N-dimethyl aminophenyl residuals in DCM by the basically donor-stronger julolidine residuals (DCJ dye), the long-waved absorption bands shift, and parallel to this, the emission bands also shift bathochromically in relation to DCM. When using DCJ in electro-luminescent devices, the visual color impression then also corresponds to a more intensive red.

The disadvantageous aggregation tendency in the application range of the doping agent >1% by weight in relation to $AlQ_3$, however, also continues to exist here, so that these materials generate too little efficiency in electro-luminescence devices. Moreover, reference should be made to poor vaporization ability of the combination with the use of DCJ. The high degradation rate during the vaporization process chiefly leads to problems in manufacturing the luminescent layer itself.

The introduction of branched tartrate-butyl substituents in the 2-position of the pyran ring of corresponding DCM analogous dyes, as mentioned in U.S. Pat. No. 5,935,720, to be sure diminishes the aggregation tendency, for example, of the dyes DCJT and DCJTB in relation to DCJ or DCM, whereby, however, even this cannot be sufficiently suppressed in order to make available materials for full-color capacity applications.

The objective of the invention was to make available an organic, red electro-luminescent device with improved quantum efficiency and improved long term stability and at the same time to develop new luminescent compounds and new doping agents for known luminescent compounds for the luminescent layer, especially for $AlQ_3$. A further objective was readying new compounds.

The organic electro-luminescent device consists, in the simplest case, of an interlaminar bonding in accordance with FIG. 1, designed with a metal electrode 1 (cathode), a luminescent layer 2, which in addition to an organic luminescent compound, which is in particular AlQ$_3$, contains at least one organic doping agent, a hole transport layer 3 which contains an organic hole transport compound, a transparent conductive anode 4, as well as a support 5 of glass or a similar transparent material.

The characteristics of this device can be optimized by a different type of construction of the electro-luminescent device, as for example according to FIGS. 2 and 3.

In accordance with the invention, the electro-luminescent device consists of a hole transport layer and a luminescent layer between two conductive electrodes, whereby at least one electrode is transparent, characterized in that the luminescent layer contains, as a doping agent for a luminescent compound, at least one compound of general formula I

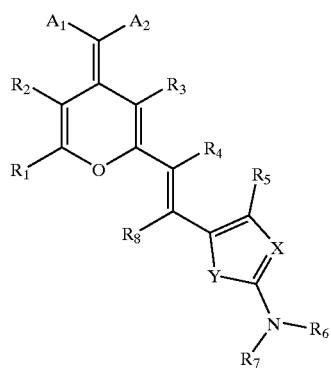

I wherein $R_1$ to $R_{12}$ are identical or different, and indicate hydrogen, straight chain or branched $C_1$–$C_6$ alkyl, aralkyl, aryl or substituted aryl;

$R_1$ and $R_2$ and/or $R_3$ and $R_4$ and/or $R_4$ and $R_5$ and/or $R_5$ and $R_{11}$ and/or $R_8$ and $R_5$ and/or $R_4$ and $R_{12}$ can form, preferably, a 5 or 6 member alicyclic, heterocyclic or aromatic ring;

$R_5$ can furthermore be hydrogen, OH, OR$_9$, N,N-di-($C_1$–$C_6$)alkylamino, acetylamino or a halogen;

$R_6$ and $R_7$ together can form an alicyclic or heterocyclic ring;

$A_1$ and $A_2$ are identical or different and are —CN, —NO$_2$ or —COOR$_{10}$;

$R_1$, $R_2$, $R_3$, $R_4$ and/or $R_8$ can, moreover be halogens, especially fluorine;

X is —CH, —CR$_{11}$ or N; and

Y is O, —NH, —NR$_{12}$, S or Se.

One invention design consisting of a luminescent layer contains at least one compound in which the substituents $R_1$ and $R_2$ or $R_3$ and $R_4$ or $R_1$ and $R_2$ and $R_3$ and $R_4$ form a carbocyclic 5 or 6 member ring as doping substance or mixed with additional other doping substances for luminescent compounds, Another invention design consisting of a luminescent layer contains, as a doping agent for a luminescent compound or mixed with additional doping agents of a different type for luminescent compounds, at least one compound of general formula II:

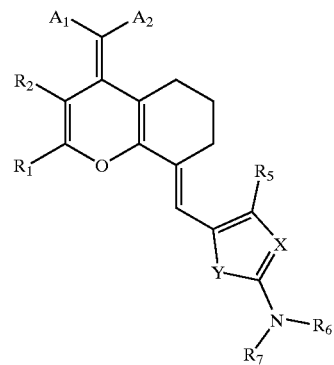

II wherein $R_1$, $R_2$, $R_5$ to $R_7$ could be equal to or variously H, straight chain or branched $C_1$–$C_6$-alkyl, especially isopropyl or tert butyl;

$R_1$ and $R_2$ can form an alicyclic, heterocyclic or aromatic, preferably 5 or 6 member ring;

$R_1$, $R_2$, $R_5$, $R_6$, $R_7$ can be equal to or variously aryl or substituted aryl;

$R_5$ can be equal to OH, OR$_8$, N,N-dialkylamino ($C_1$–$C_6$), acetylamino, or a halogen;

$R_6$ and $R_7$ can jointly form an alicyclic or heterocyclic ring;

$A_1$, $A_2$ can be equal to or variously CN, NO$_2$ or COOR$_5$;

$R_8$ is H, straight chained or branched $C_1$–$C_6$ or aryl;

X is equal to CH, CR$_5$ or N;

Y is equal to O, NH, NR$_8$, S or Se.

An additional invention design consisting of a luminescent layer as doping agent for luminescent compounds or mixed with further doping agents of a different type for luminescent compounds, contains at least one compound of general formula III:

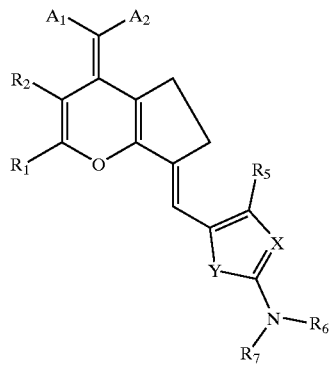

III wherein $R_1$, $R_2$, $R_5$ to $R_7$ can be equal to or various H, straight chain or branched $C_1$–$C_6$ Alkyl, especially isopropyl or tert butyl;

$R_1$ and $R_2$ can form an alicyclic, heterocyclic or aromatic, preferably 5 or 6 member ring;

$R_1$, $R_2$, $R_5$, $R_6$, $R_7$ can be equal to or various aryl or substituted aryl;

$R_5$ can be equal to OH, $OR_8$, N,N-dialkylamino (C1–C6), acetylamino, or a halogen;

$R_6$ and $R_7$ can jointly form an alicyclic or heterocyclic ring;

$A_1$, $A_2$ can be equal to or various CN, $NO_2$ or $COOR_8$;

$R_8$ is H, straight chained or branched $C_1$–$C_6$ or aryl;

X is equal to CH, $CR_5$ or N; and

Y is equal to O, NH, $NR_8$, S or Se.

A further invention design consisting of a luminescent layer contains, as doping agent for a luminescent compound or mixed with further doping agents of a different type, at least one compound of general formula IV:

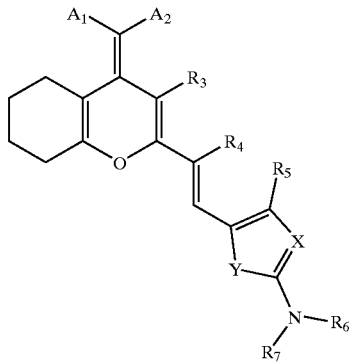

IV wherein $R_3$ to $R_7$ can be equal to or various H, straight chain or branches $C_1$–$C_6$ alkyl, especially isopropyl or tert butyl;

$R_3$ and $R_4$ can form an alicyclic, heterocyclic or aromatic, preferably 5 or 6 member ring;

$R_5$, $R_6$, $R_7$ can be equal to or various aryl or substituted aryl;

$R_5$ can be equal to OH, $OR_8$, N,N-dialkylamino (C1–C6), acetylamino, or a halogen;

$R_6$ and $R_7$ can jointly form an alicyclic or heterocyclic ring;

$A_1$, $A_2$ can be equal to or various CN, $NO_2$ or $COOR_8$;

$R_8$ is H, straight chained or branched $C_1$–$C_6$ or aryl;

X is equal to CH, $CR_5$ or N;

Y is equal to O, NH, $NR_8$, S or Se.

An additional invention design consisting of a luminescent layer, as a doping agent or mixed with additional doping agents for luminescent compounds of a different type, contains at least one compound of general formula V:

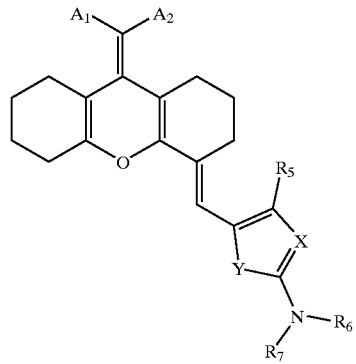

V wherein $R_5$ to $R_7$ can be equal to various aryl, substituted aryl, hydrogen, straight chain or branched $C_1$–$C_6$ aryl; $R_5$ in particular can be isopropyl or tert butyl;

$R_5$ can be equal to OH, $OR_8$, N,N-dialkylamino (C1–C6), acetylamino, or a halogen;

$R_6$ and $R_7$ can jointly form an alicyclic or heterocyclic ring;

$A_1$, $A_2$ can be equal to or various CN, $NO_2$ or $COOR_8$;

$R_8$ is H, straight chained or branched $C_1$–$C_6$ or aryl;

X is equal to CH, $CR_5$ or N;

Y is equal to O, NH, $NR_8$, S or Se.

When $R_1$, $R_2$, $R_5$ or $R_7$ have the meaning of aryl, it is preferably cyclohexyl or phenyl. Preferably 1 to 3 substituents for this are in particular $C_1$–$C_6$ alkyl, special methyls, isopropyls or tert butyls.

If $R_6$ and $R_7$ form a heterocyclic ring, a preferred heteroatom is O. Further hetero-atoms can be N or S.

A further invention design consisting of a luminescent layer, as a doping agent or mixed with further doping agents for luminescent compounds of a different type, contains at least one compound for which $A_1$ and $A_2$ mean —CN in each case.

Preferably, the residual $R_1$ to $R_{12}$ in the meaning of $C_1$–$C_6$ alkyl represent methyl, isopropyl or tartan butyl in any given case.

An additional invention design according to the invention, consisting of a concentration of a doping agent mixed with another doping agent, according to the invention, or with a known doping agent of luminescent substances in the luminescent layer can be varied in the range between 0.1% by weight and 50% by weight in relation to the total weight of all doping agents.

Furthermore, it is preferable that the luminescent layer contains $AlQ_3$ as a luminescent compound.

It was found that the new and known compounds recently used in electro-luminescent devices in the concentration range of >1% by weight to 8% by weight, preferably >1 to 5% by weight, and specifically 1.5–3% by weight in relation to the weight of the organic luminescent compound $AlQ_3$ generate a very efficient pure red light alone or together with $AlQ_3$.

Objects of the invention are also new compounds of general formula I

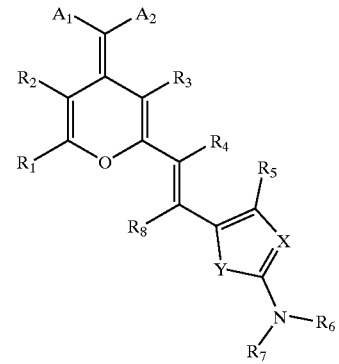

I wherein $R_1$ to $R_{12}$ are equal to or different and mean hydrogen, straight chain or branched $C_1$–$C_6$ alkyl, aralkyl, aryl or substituted aryl;

$R_1$ and $R_2$ and/or $R_3$ and $R_4$ and/or $R_4$ and $R_5$ and/or $R_5$ and $R_{11}$ and/or $R_8$ and $R_5$ and/or $R_4$ and $R_{12}$ can form a preferably 5 or 6 member alicyclic, heterocyclic or aromatic ring;

$R_5$ can furthermore be hydrogen, OH, $OR_9$, N,N-di-($C_1$–$C_6$) alkylamino, acetylamino or halogen;

$R_6$ and $R_7$ together can form an alicyclic or heterocyclic ring;

A₁ and A₂ are identical or different and are —CN, —NO₂ or —COOR₈;
X is —CH, —CR₁₁ or N; and
Y is O, —NH, —NR₁₂, S or Se, provided that Y is not S if X means N and R₅ means aryl.

The device to be used in accordance with the invention is produced according to the state of the art technology in that one, first of all, installs the anode as a transparent conductive layer of indium-tin oxide (ITO) in a layer thickness from 10 nm to 200 nm on a stable glass substrate. Immediately before applying the organic layers, this ITO layer, especially following long storage, is to be treated in an ultrasound bath successively with pure acetone and methanol. After blowing off insoluble particles with a beam of vaporization capable CO₂ ice crystals, the layer is subsequently additionally treated with an oxygen plasma, whereby organic impurities are burned and eliminated.

Likewise according to the state of the art technology, one can manufacture the hole transport layer 3 (HTL) using the spin coating technique. The hole transport layer 3 consists in this case, for example, of a molecular dispersion of N,N'-diphenyl-N,N'-bis-(3-methylphenyl)-1,1'-biphenyl-4,4'-diamine (TPD), in poly-(N-vinylcarbazole) (PVK) or a suitable polycarbonate in the proportion by weight of 1:1, whereby the ratio of hole transport material to hole transporting binding agents or also to an insulating binding agent, such as, for example, polycarbonate, can be varied in wide range. First a clear solution of PVK/TPD is produced, according to generally known principles, in an organic solvent or solvent mixture, as for example, methylene chloride in a dissolving vessel while stirring under inert gas at room temperature. The electrically conductive transparent substrate is subsequently coated by means of a spin coating device to the extent that the hole transport layer 3 possesses, following drying at 25E C to 40E C under inert gas, for example, in a vacuum drying chamber, a dry layer thickness from 50 to 80 nm. It should be mentioned that the hole transport layer 3 according to the state of the art technology, preferably consisting of N,N'-diphenyl-N,N'-bis-(3-methylphenyl)-1,1'-biphenyl-4,4'-diamine (TPD) or N,N'-biphenyl-N,N'-bis-(1-naphthyl)-benzidine (1-NPB), can also be vapor deposited on the conductive support.

Subsequently, a compound described in accordance with the invention can be applied under a high vacuum individually or also as a mixture with other types of doping agents using the co-vapor deposition technique together with the luminescent compound, for example, together with AlQ₃. Here the concentration of the doping agent or also of a doping agent mixture in relation to the overall amount of material to be vaporized can come to between 1% by weight and 5% by weight, especially with a concentration between 1.5% by weight and 3% by weight in the case where AlQ₃ is used as a luminescent substance to emit a red light.

The concentration of the other type of doping agent in the case where a mixture of doping agents is used can here, according to the purpose for using the electro-luminescent device, be varied in a wide range, for example between 0.1% by weight and 50% by weight in relation to the overall amount of all doping agents.

Surprisingly, with the accomplishment of the objective of the invention, it was found that, as a collateral effect, the organic electro-luminescent device emits white light in the event of an "underdoping" of the luminescent compound, especially with an "underdoping" of AlQ₃ with the doping agents used in accordance with this invention.

Underdoping exists when the doping agent is co-vaporized alone or mixed with other types of doping agents in a concentration between 0.1% and 1% by weight, especially between 0.2% and 0.8% by weight in relation to the overall amount of material to be vaporized.

Without interim ventilation, the metal cathode 1 is finally applied by vaporization of LiF or Li benzoate and Al, usually in a proportion of 10:1 (0.7 nm Li benzoate+100 nm Al). But other metals or alloys, or other proportions of metals or alloys, can also be used.

One will obtain very efficient red electro-luminescent devices when, in the luminescent layer 2, preferably in the following compounds 1 to 18 in the table, they are used as new, previously unknown doping agents, individually or also mixed with other suitable doping agents for doping AlQ₃ or other luminescent compounds (the proportion of doping substances of the same time can here be freely selected):

TABLE

1 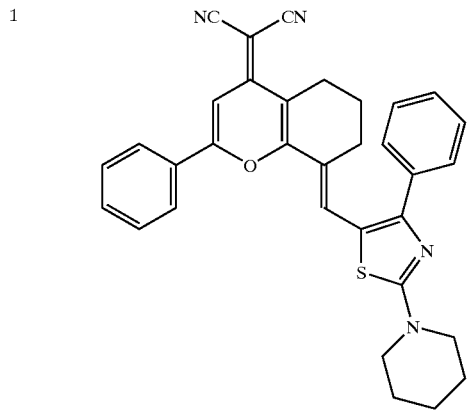

2 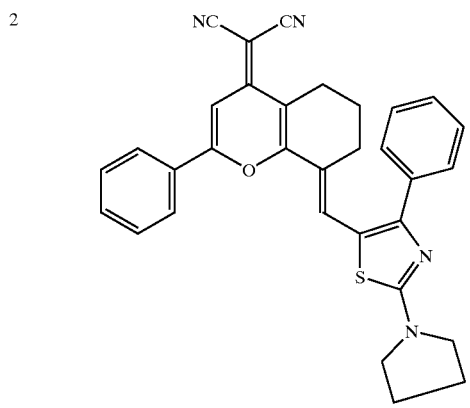

3 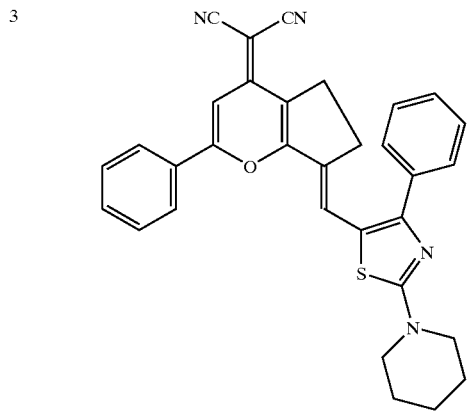

TABLE-continued
| | |
|---|---|
| 4 | 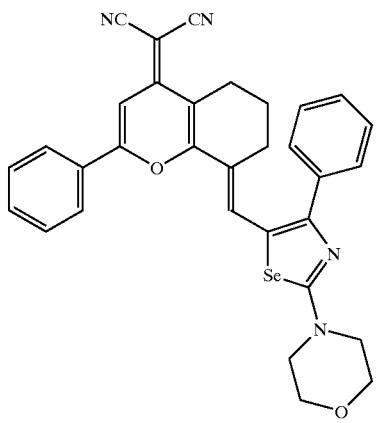 |
| 5 | 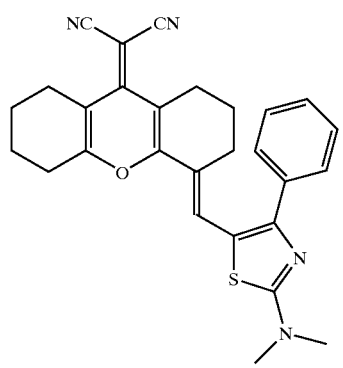 |
| 6 | 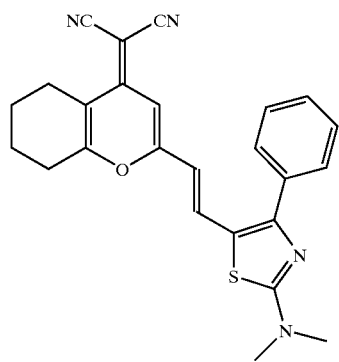 |
| 7 | 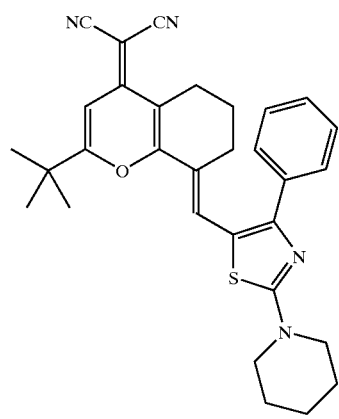 |
TABLE-continued
| | |
|---|---|
| 8 | 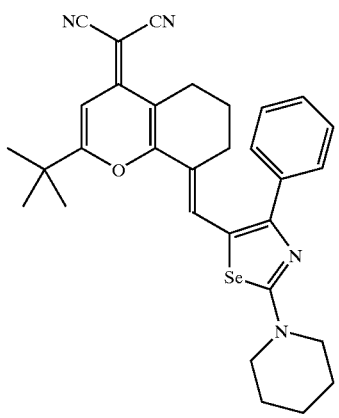 |
| 9 | 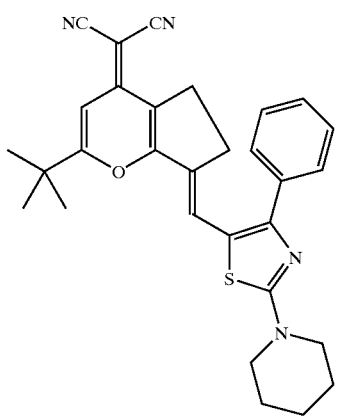 |
| 10 | 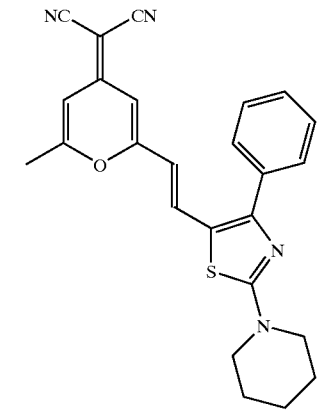 |

TABLE-continued
| 11 | 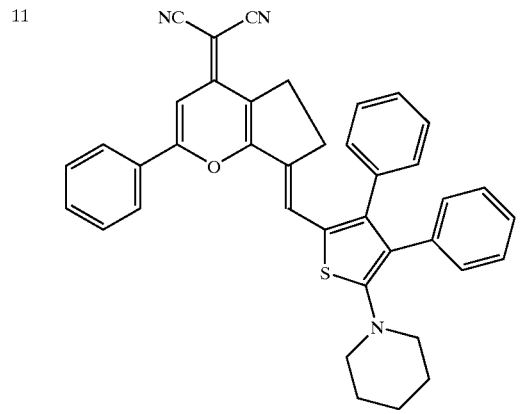 |
| --- | --- |
| 12 | 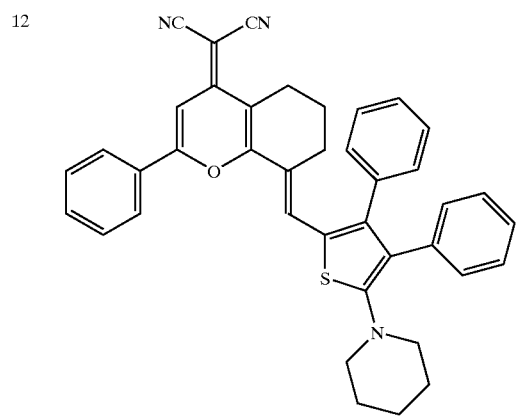 |
| 13 | 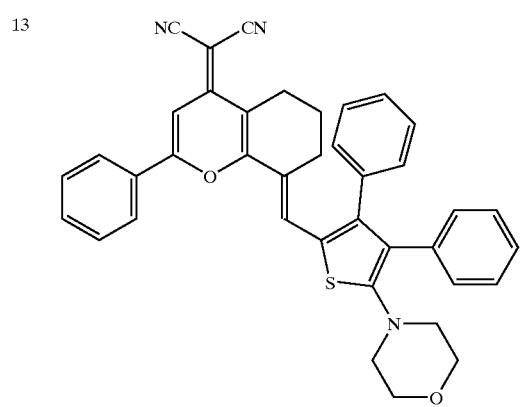 |
| 14 | 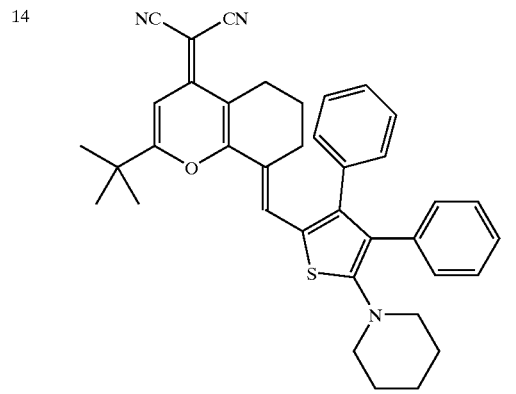 |see 
TABLE-continued
| 15 | 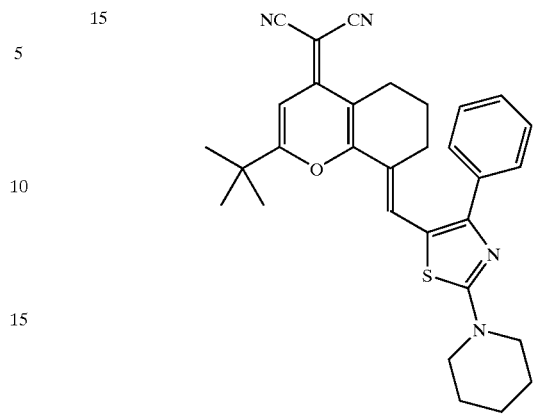 |
| --- | --- |
| 16 | 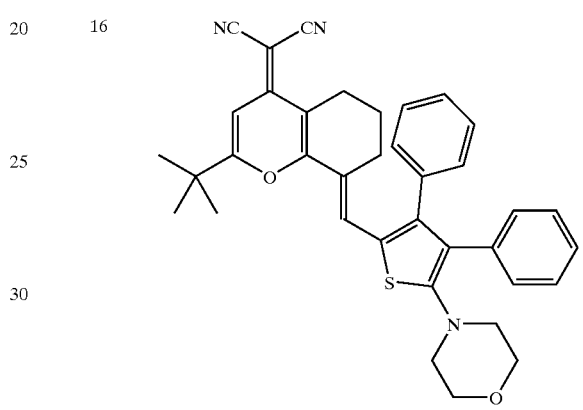 |
| 17 | 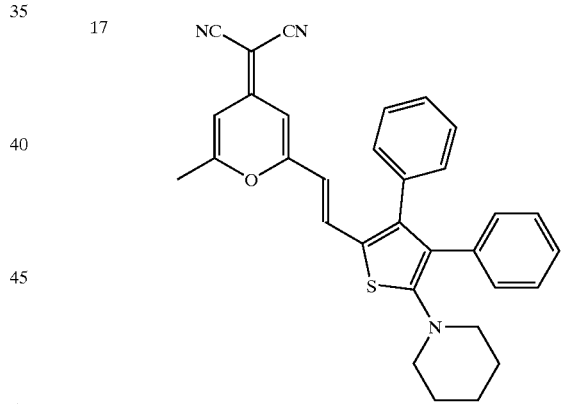 |
| 18 | 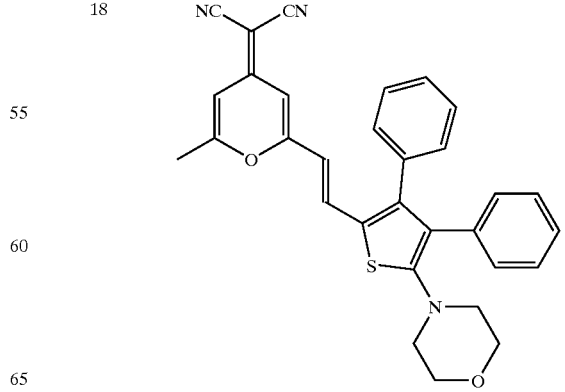 |

One moreover will obtain very efficient red luminescent devices if the new doping agents or also mixtures of these with another type of doping agent (for example, dyes according to U.S. Pat. No. 4,769,292) are co-vaporized for manufacturing the luminescent layer, such as with a 1,2 or 1,3-substituted quadratic acid dye.

Dyes which in accordance with the invention are used as doping agents for luminescent compounds are known as such and described in DE U.S. Pat. No. 2,831,054 and elsewhere for producing images according to a photoelectrophoretic procedure.

With these procedures, charged particles are transported in an electric field through graphic exposure of an electrically charged device containing a dye which then supplies a positive or negative image of the pattern. This method is of a completely different type in relation to the manufacture of electro-luminescent devices with dyes used in accordance with the invention and therewith not tangent.

The general manufacturing method of compounds of this dye is disclosed in U.S. Pat. No. 2,965,486.

The following examples should serve to explain the invention in greater the invention is not only restricted to these.

Figure 1:
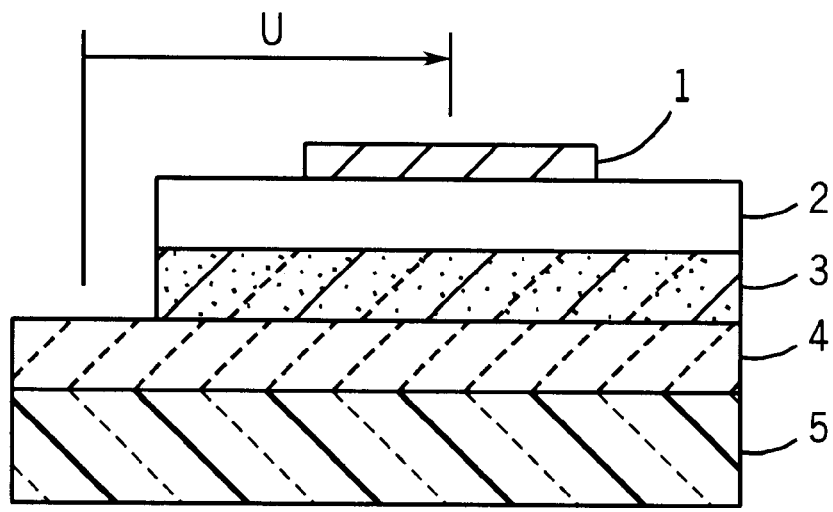
FIG. 1 Depicts a simple layer structure of an electro-luminescent device

In the drawings, U shows the voltage applied between the corresponding electrodes.

EXAMPLE OF A SYNTHESIS

The manufacture of the dyes to be used takes place preferably in a "stew reaction" according to the known methods (see U.S. Pat. No. 2,985,486 of U.S. Pat. No. 5,908,581) on basis of a reactive 2-methyl-4H-pyran-4-onanes by condensation, first with malonitrile in acetic acid anhydride and, in a subsequent reaction with appropriate hetero-aromatic aldehydes without isolation of the 4-dicyanomethylene-2-methyl-4-pyrans first formning. The hetero-aromatic aldehydes necessary for the synthesis and their fundamental substances are obtained according to known reaction procedures in accordance with S. Scheithauer et al. in Z. Chem. 8(1968) 182; Hartmann, H. J. Prakt. Chem. 36 (1967) 50; Liebscher, J. Houben Weyl, Methods of Organic Chemistry Vol. E 8b, Stuttgart 1995 and Organikum, Basic Practical Organic Chemistry Course, 13$^{th}$ edition, VEB German Sciences Publishing Company, Berlin 1974.

Example 1

Pursuant to FIG. 1, a hole transport layer (HTL) 3 is applied on a glass support 5 coated with ITO (indium-zinc oxide) 4 by spin coating a solution of N,N'-diphenyl-N,N'-bis-(3-methylphenyl)-benzidine mixed with poly-(N-vinyl carbazole) 1:1 (parts by weight) in dichloromethane. After drying the layer under inert gas at a temperature between 25° C. and 40° C., the layer thickness becomes 50 nm. Then the luminescent layer 2 is applied to the obtained hole transport layer 3 in a high vacuum ($10^{-5}$ hPa) by co-vaporization of $AlQ_3$ and the purified dye 1 in a concentration of 1.8% by weight in relation to $AlQ_3$. Subsequently the metal cathode 1 is applied to the 60 nm thick luminescent layer 2 by vaporization of LiF and Al (0.7 nm LiF+100 nm Al).

To measure the electro-luminescence, a controllable tension between 1 and 20 V is applied between the ITO and metal electrode. The electro-luminescent device so obtained shows a luminance up to 400 cd/$M^2$ at 12.5 V. The emitted light is free from concurrent emissions of $AlQ_3$ in the region around 530 nm and shows visually a pure red color tone.

Example 2

Vapor deposit a hole transport layer (HTL) 3 of N,N'-diphenyl-N,N'-bis-(3-methylphenyl)-benzidine to a glass support 5 in accordance with FIG. 1 coated with ITO (indium-tin oxide) 4 in a layer thickness of 50 nm in a high vacuum ($10^{-5}$ hPa). Then apply the luminescent layer 2 to the hole transport layer 3 obtained by co-vaporization of $AlQ_3$ and the purified dye 1 in a concentration of 2.2% by weight in relation to $AlQ_3$. The thickness of the vapor deposited luminescent layer 2 comes to 60 nm. Subsequently metal cathode 1 is applied by vaporization of Li benzoate and Al (0.7 nm Li benzoate+100 nm Al).

To measure the electro-luminescence, a controllable tension between 1 and 20 V is applied between the ITO and metal electrode. The electro-luminescent device so obtained shows a luminance up to 450 cd/$m^2$ at 12.5 V. The emitted light is free from concurrent emissions of $AlQ_3$ in the region around 530 nm and shows visually a pure red color tone.

Example 3

Figure 2:
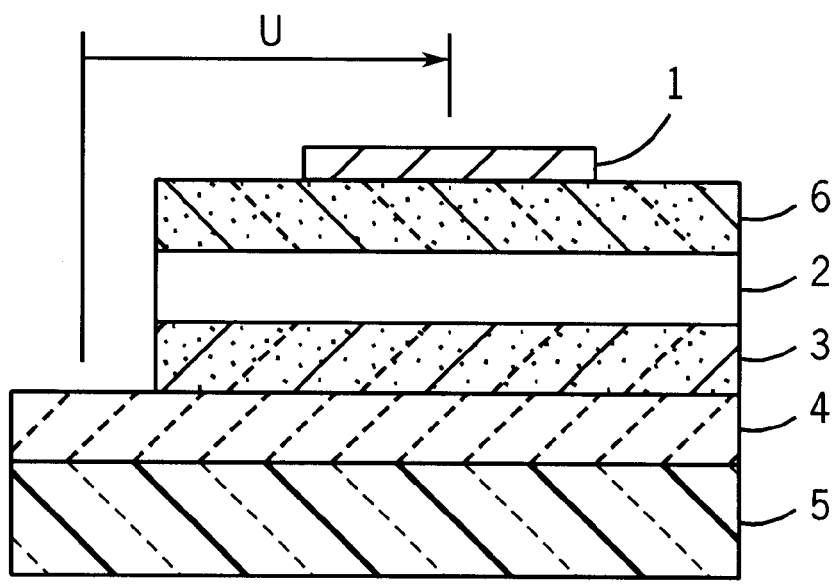
FIG. 2 Shows the layer structure with an additional electron transport layer
Figure 3:
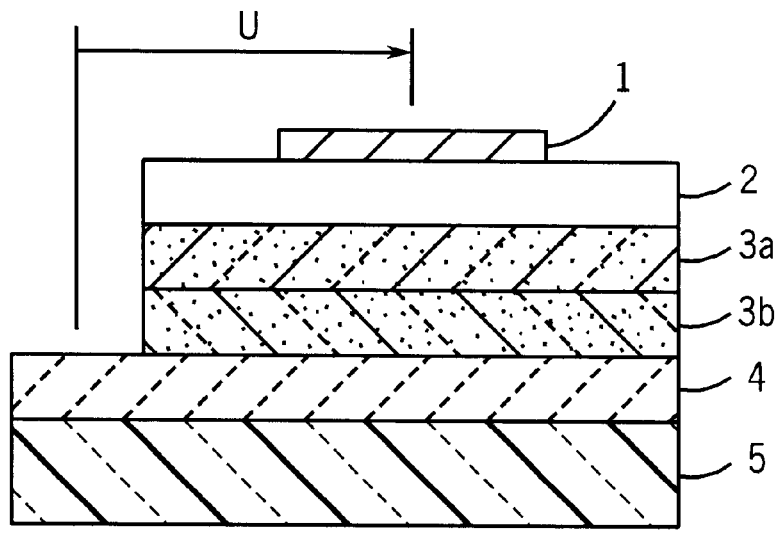
FIG. 3 Illustrates the layer structure with an additional hole transport layer

Vapor deposit a hole transport layer (HTL) 3 of 4,4',4"-tris-(N-(1-naphthyl)-N-phenyl-amino)-triphenylamine to a glass support 5 coated with ITO (indium-tin oxide) 4 in accordance with FIG. 2 in a layer thickness of 55 nm in a high vacuum ($10^{-5}$ hPa). Apply the luminescent layer 2 to the hole transport layer 3 so obtained by co-vaporization of $AlQ_3$ and the purified dye 1 in a concentration of 1.8% by weight in relation to $AlQ_3$. The thickness of the vapor deposited luminescent layer 2 comes to 40 nm. Then apply to this layer 10 nm $AlQ_3$ as electron transport layer 6. Subsequently apply metal cathode 1 by vaporization of Li benzoate and Al (0.7 nm Li benzoate+100 nm Al).

To measure the electro-luminescence, a controllable tension between 1 and 20 V is applied between the ITO and metal electrode. The electro-luminescent device so obtained shows a luminance up to 1000 cd/$m^2$ at 12.5 V. The emitted light is free from concurrent emissions of $AlQ_3$ in the region around 530 nm and shows visually a pure red color tone.

Example 4

Figure 4:
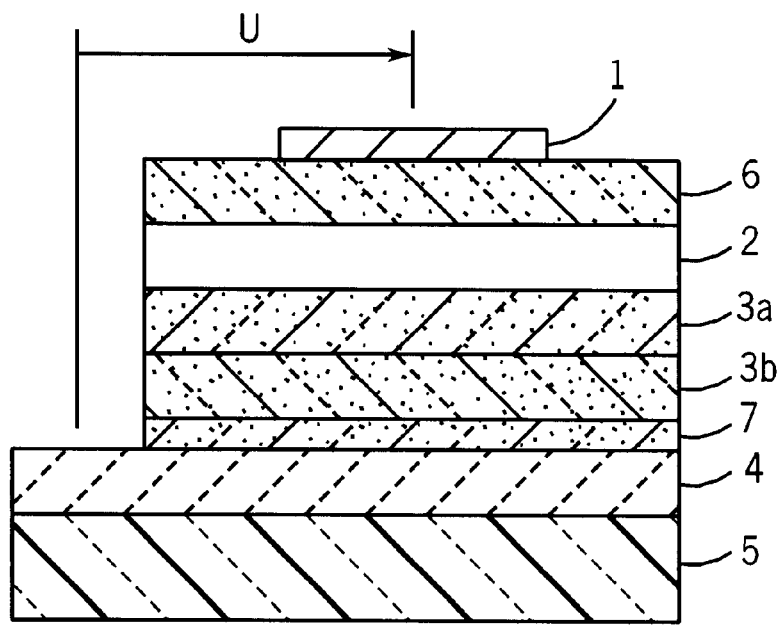
FIG. 4 Represents the layer structure with an additional hole injection layer.

Sequentially vapor deposit a 5 nm thick hole injection layer of CuPC, a hole transport layer (HTL) 3b of 4,4',4"-tris-(N-(1-naphthyl)-N-phenyl-amino)-triphenyl amine to a purified glass support 5 coated with ITO (indium-tin oxide) 4 in accordance with FIG. 4 in a layer thickness of 55 nm and an additional hole transport layer 3a of N,N'-biphenyl-N, N'-bis-(1-naphthyl) benzidine (1-NPB) in a layer thickness of 5 nm in a high vacuum ($10^{-5}$ hPa). Then apply the luminescent layer 2 to the hole transport layers 3a, 3b by co-vaporization of $AlQ_3$ and purified dye 1 in a concentration of 2.2% by weight in relation to $AlQ_3$. The thickness of the vapor deposited luminescent layer 2 comes to 40 nm. Then vapor deposit 5 nm of $AlQ_3$ as an electron transport layer 6 to this layer. Subsequently apply metal cathode 1 by vaporization of Li benzoate and Al (0.7 nm Li benzoate+100 nm Al).

To measure the electro-luminescence, a controllable tension between 1 and 15 V is applied between the ITO and metal electrode. The electro-luminescent device so obtained shows a luminance up to 2050 cd/$M^2$ at 14.0 V. The emitted light is free from concurrent emissions of $AlQ_3$ in the region around 530 nm and shows visually a pure red color tone.

Example 5

Apply luminescent layer 2 by co-vaporization of $AlQ_3$ and dye 1 to hole transport layers 3a, 3b analogously to the layer structure of example 4, whereby this is used in a concentration of only 0.7% by weight (underdoping) in relation to AlQ$_3$. One will obtain an electro-luminescent device which alternatively emits white light when a voltage of 17 V is applied between ITO and metal electrode.

Example 6

Vapor deposit a 5 nm thick hole injection layer of CuPC, a hole transport layer (HTL) 3b of 4,4',4"-tris-(N-(1-naphthyl)-N-phenyl-amino)-triphenylamine to a purified glass support 5 coated with ITO (indium-tin oxide) 4 in accordance with FIG. 4 in a layer thickness of 55 nm and a further hole transport layer 3a of 1-NPB in a layer thickness of 5 nm in a high vacuum ($10^{-5}$ hPa) one after the other. Then apply the luminescent layer 2 to the hole transport layers 3a, 3b so obtained by co-vaporization of AlQ$_3$ and the purified dye 2 in a concentration of 2.5% by weight in relation to AlQ$_3$. The thickness of the vapor deposited luminescent layer 2 amounts to 40 nm. Then vapor deposit on this layer 5 rim of AlQ$_3$ as an electron transport layer 8. Subsequently apply metal cathode 1 by vaporization of Li benzoate and Al (0.7 nm Li benzoate+100 nm Al).

To measure the electro-luminescence, a controllable tension between 1 and 15 V is applied between the ITO and metal electrode. The electro-luminescent device so obtained shows a luminance of up to 2200 cd/m$^2$ at 13.8 V. The emitted light is free from concurrent emissions of AlQ$_3$ in the region around 530 nm and shows visually a pure red color tone.

What is claimed is:

1. An electro-luminescent device, comprising a hole transport layer and a luminescent layer between two conductive electrodes, wherein the luminescent layer comprises, as a luminescent compound or doping agent for a luminescent compound, at least one compound of formula I:

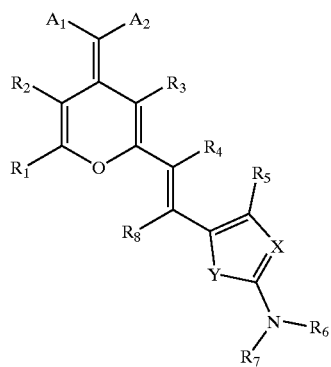

I wherein $R_1$, $R_2$, $R_3$, $R_4$, and $R_8$ are identical or different and are hydrogen, straight chain or branched $C_1$–$C_6$-alkyl, aralkyl, aryl, substituted aryl, or halogen; $R_5$ is hydrogen, $OR_9$, N,N-di-($C_1$–$C_6$)alkylamino, acetylamino, straight chain or branched $C_1$–$C_6$ alkyl, aralkyl, aryl, substituted aryl, or halogen; or one or more of substituent pairs $R_1/R_2$, $R_3/R_4$, $R_4/R_5$, and $R_5/R_8$ link together to form a 5 or 6 member alicyclic, heterocyclic, or aromatic ring;

$R_6$ and $R_7$ are identical or different and are hydrogen, straight chain or branched $C_1$–$C_6$ alkyl, aralkyl, aryl, or substituted aryl; or $R_6$ and $R_7$ link together to form a heterocyclic ring;

$A_1$ and $A_2$ are identical or different and are —CN, —NO$_2$, or —COOR$_{10}$;

X is —CR$_{11}$, or N;

Y is O, —NR$_{12}$, S, or Se; and $R_9$ to $R_{12}$ are identical or different and are hydrogen, straight chain or branched $C_1$–$C_6$ alkyl, aralkyl, aryl, or substituted aryl; or one or more of substituent pairs $R_5/R_{11}$ and $R_4/R_{12}$ link together to form a 5 or 6 member alicyclic, heterocyclic, or aromatic ring.

2. The device according to claim 1, wherein the luminescent layer comprises a luminescent compound and a doping agent, which comprises a compound of formula I in which one or more of the substituent pairs $R_1/R_2$ and $R_3/R_4$ link together to form a carbocyclic 5 or 6 member ring.

3. The device according to claim 1, wherein the compound of formula I includes at least one compound of formula II:

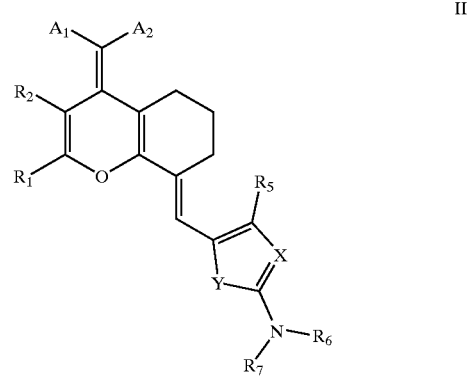

II wherein $R_1$, $R_2$, $R_5$, $R_6$, $R_7$, $A_1$, $A_2$, X, and Y are as defined in claim 1.

4. The device according to claim 1, wherein the compound of formula I includes at least one compound of formula III:

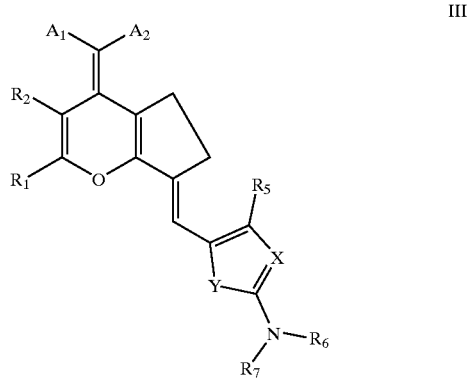

III wherein $R_1$, $R_2$, $R_5$, $R_6$, $R_7$, $A_1$, $A_2$, X, and Y are as defined in claim 1.

5. The device according to claim 1, wherein the compound of formula I includes at least one compound of formula IV:

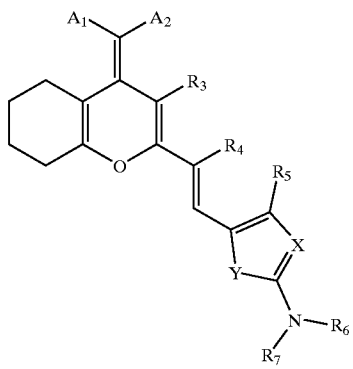

wherein $R_3$, $R_4$, $R_5$, $R_6$, $R_7$, $A_1$, $A_2$, X, and Y are as defined in claim 1.

6. The device according to claim 1, wherein the compound of formula I includes at least one compound of formula V:

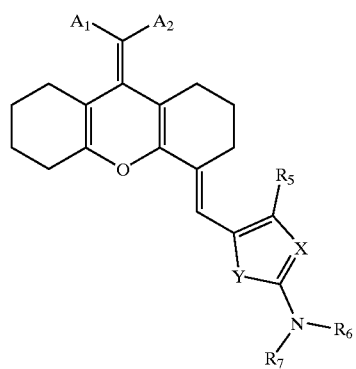

wherein $R_5$, $R_6$, $R_7$, $A_1$, $A_2$, X, and Y are as defined in claim 1.

7. The device according to claim 1, wherein the straight chain or branched chain $C_1$–$C_6$-akyl substituents are the same or different and are methyl, isopropyl, or tert-butyl.

8. The device according to claim 1, wherein the luminescent layer comprises a luminescent compound and a doping agent, which includes at least one compound of the formula I; and the luminescent layer has a concentration of the doping agent between 1% by weight and 5% by weight in relation to the amount of the luminescent compound.

9. The device according to claim 8, wherein the luminescent layer has a concentration of the doping agent between 1.5% by weight and 3% by weight in relation to the amount of the luminescent compound.

10. The device according to claim 8, wherein the luminescent compound comprises $AlQ_3$.

11. The device according to claim 8, wherein the device generates a pure red light emission.

12. The device according to claim 1, wherein $A_1$ and $A_2$ are —CN.

13. The device according to claim 1, wherein the luminescent layer comprises a luminescent compound and a doping agent; and the doping agent includes at least one compound of the formula I and a doping agent of a different type.

14. The device according to claim 1, wherein the luminescent layer comprises $AlQ_3$ and a doping agent, which includes at least one compound of the formula I.

15. The device according to claim 14, wherein the luminescent layer has a concentration of the doping agent from 0.1 to 1% by weight in relation to the weight of the $AlQ_3$.

16. The device according to claim 14, wherein the device generates a white light.

17. A compound having formula I:

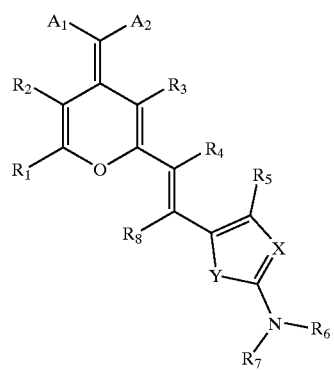

wherein $R_1$, $R_2$, $R_3$, $R_4$, and $R_8$ are identical or different and are hydrogen, straight chain or branched $C_1$–$C_6$-alkyl, aralkyl, aryl, substituted aryl, or halogen; $R_5$ is hydrogen, —$OR_9$, N,N-di-($C_1$–$C_6$)alkylamino, acetylamino, straight chain or branched $C_1$–$C_6$ alkyl, aralkyl, aryl, substituted aryl, or halogen; or one or more of substituent pairs $R_1/R_2$, $R_3/R_4$, $R_4/R_5$, and $R_5/R_8$ link together to form a 5 or 6 member alicyclic, heterocyclic, or aromatic ring;

$R_6$ and $R_7$ are identical or different and are hydrogen, straight chain or branched $C_1$–$C_6$ alkyl, aralkyl, aryl, or substituted aryl; or $R_6$ and $R_7$ link together to form a heterocyclic ring;

$A_1$ and $A_2$ are identical or different and are —CN, —$NO_2$, or —$COOR_{10}$;

X is —$CR_{11}$, or N;

Y is O, —$NR_{12}$, S, or Se; and $R_9$ to $R_{12}$ are identical or different and are hydrogen, straight chain or branched $C_1$–$C_6$-alkyl, aralkyl, aryl, or substituted aryl; or one or more of substituent pairs $R_5/R_{11}$, and $R_4/R_{12}$ link together to form a 5 or 6 member alicyclic, heterocyclic, or aromatic ring.

18. The compound according to claim 17, wherein the compound has formula II:

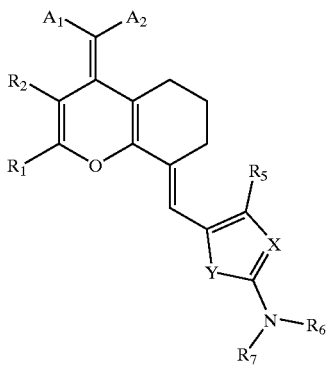

wherein $R_1$, $R_2$, $R_5$, $R_6$, $R_7$, $A_1$, $A_2$, X, and Y are as defined in claim 17.

19. The compound according to claim 17, wherein the compound has formula III:

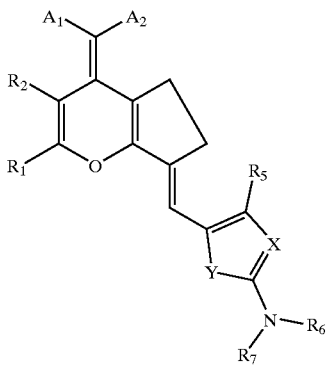

wherein $R_1$, $R_2$, $R_5$, $R_6$, $R_7$, $A_1$, A2, X, and Y are as defined in claim 17.

20. The compound according to claim 17, wherein the compound has formula IV:

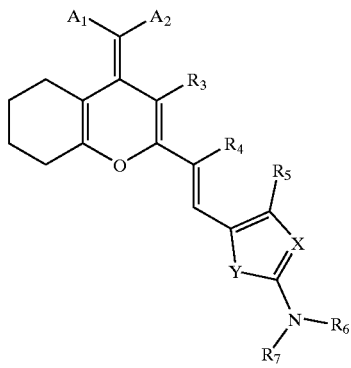

wherein $R_3$, $R_4$, $R_5$, $R_6$, $R_7$, $A_1$, $A_2$, X, and Y are as defined in claim 17.

21. The compound according to claim 17, wherein the compound has formula V:

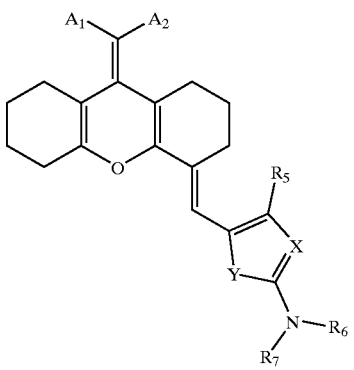

wherein $R_5$, $R_6$, $R_7$, $A_1$, $A_2$, X, and Y are as defined in claim 17.

22. The compound according to claim 17, wherein $A_1$ and $A_2$ are —CN.

23. The compound according to claim 17, wherein $R_6$ and $R_7$ link together to form a heterocyclic ring.

24. The compound according to claim 23, wherein

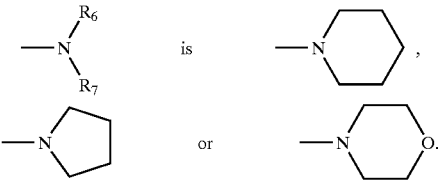

25. The compound according to claim 17, wherein X is N; and Y is S.

26. The compound according to claim 17, wherein X is C—$R_{11}$ and $R_{11}$ is aryl or substituted aryl; and Y is S.

27. The compound according to claim 17, wherein one or more of the substituent pairs $R_1/R_2$ and $R_3/R_4$ link together to form a 5 or 6 member carbocyclic ring.

28. The compound according to claim 17, wherein $A_1$ and $A_2$ are —CN; X is N; Y is S; one or more of the substituent pairs $R_1/R_2$ and $R_3/R_4$ link together to form a 5 or 6 member carbocyclic ring; $R_5$ is aryl or substituted aryl; and $R_8$ is hydrogen.

29. The compound according to claim 17, wherein $A_1$ and $A_2$ are —CN; X is C—$R_{11}$ and $R_{11}$ is aryl or substituted aryl; Y is S; one or more of the substituent pairs $R_1/R_2$ and $R_3/R_4$ link together to form a 5 or 6 member carbocyclic ring; $R_5$ is aryl or substituted aryl; and $R_8$ is hydrogen.

30. The compound according to claim 17, wherein at least one of $R_1$, $R_2$, $R_3$, $R_4$, $R_5$, $R_6$, and $R_7$ is isopropyl or tert-butyl.

31. The compound according to claim 17, wherein $A_1$ and $A_2$ are —CN; $R_5$ is phenyl; $R_8$ is hydrogen; X is N; Y is S; and $R_6$ and $R_7$ are identical or different and are straight chain or branched $C_1$–$C_6$-alkyl, or $R_6$ and $R_7$ link together to form a 5 or 6 member heterocyclic ring.

* * * * *